United States Patent [19]

Lipshutz et al.

[11] 4,278,887

[45] Jul. 14, 1981

[54] FLUID SAMPLE CELL

[75] Inventors: Victor G. Lipshutz, Tarrytown; Edward Stark, Yorktown Heights, both of N.Y.

[73] Assignee: Technicon Instruments Corporation, Tarrytown, N.Y.

[21] Appl. No.: 118,563

[22] Filed: Feb. 4, 1980

[51] Int. Cl.³ .................... G01N 21/01; G01J 1/04; G01N 1/10
[52] U.S. Cl. ............................... 250/432; 356/236; 356/246
[58] Field of Search ............... 250/432, 435, 437, 438, 250/343, 341, 344, 349; 356/236, 246

[56] References Cited

U.S. PATENT DOCUMENTS

| | | | |
|---|---|---|---|
| 2,649,011 | 8/1953 | Black | 356/246 |
| 2,707,900 | 5/1955 | Maresh et al. | 356/236 |
| 3,886,364 | 5/1975 | Walker et al. | 250/343 |

*Primary Examiner*—Bruce C. Anderson
*Attorney, Agent, or Firm*—S. P. Tedesco

[57] ABSTRACT

A fluid sample cell comprising a sample compartment of precisely predetermined depth bounded by opposed surfaces of a transparent window and a diffuse mirror is disclosed, and comprises inlet and outlet ports for the flow of a series of successive samples into and through said sample compartment and the spectroscopic analysis thereof by irradiation and detection of transmitted and reflected radiation.

11 Claims, 3 Drawing Figures

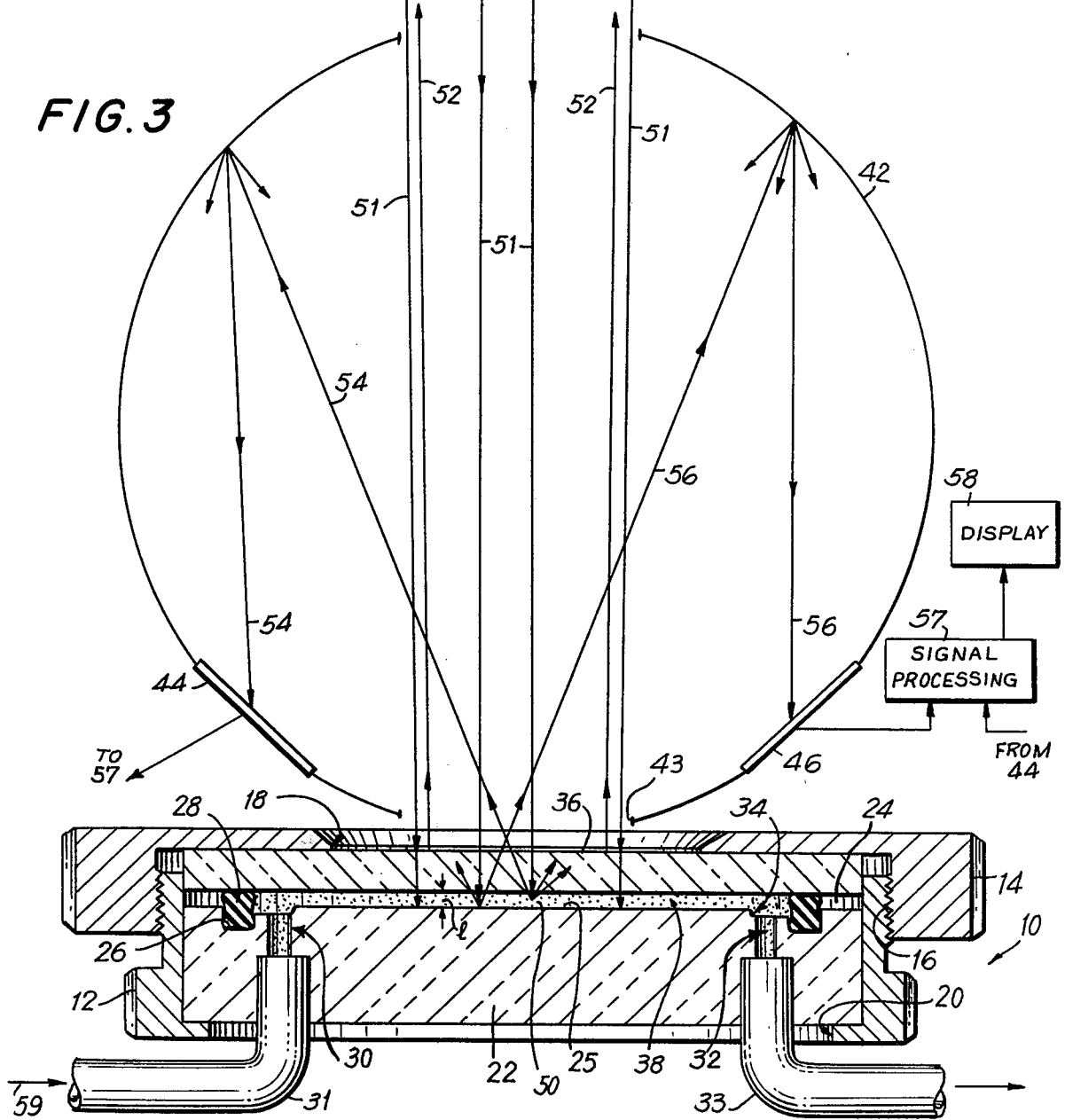

FLUID SAMPLE CELL

BACKGROUND OF THE INVENTION

1. Field of the Invention

This invention relates to a new and improved fluid sample cell for spectroscopic analysis of a wide variety of different fluid samples.

2. Description of the Prior Art

A wide variety of sample cells are known for use in accordance with conventional transmission spectroscopy techniques for analyzing fluid samples to determine the concentration of radiation energy-absorbing sample constituents. Such analysis is based on the selective attenuation of radiation energy at different predetermined wavelengths passing through the sample in accordance with the absorption characteristics of the sample, the concentration of the radiation energy-absorbing constituents of the sample, and the radiation energy transmission path length through the sample. Certain fluid samples, for example, liquids, contain suspensions of fine particles which independently attenuate radiation energy transmitted therethrough by diffusely scattering the same. Depending upon particle size distribution and concentration of particles in the fluid medium, a portion of the incident beam of light, instead of being directly transmitted therethrough, will be diffusely scattered into forward- and back-scatter components of variable geometric distribution. In conventional transmission spectroscopy, the back-scatter component, as well as a portion of the forward-scatter component, will not be sensed by the radiation sensor. The resultant loss of signal appears as part of the attenuation measurement. Variations in turbidity, therefore, will introduce a variable parameter in the measurement due to variations in the loss of the diffusely scattered components, as opposed to variations in the purely absorptive properties of the constituent of interest in the fluid.

Furthermore, the spectral energy attenuation characteristics of true solutions is a logarithmic function of molecular concentration, whereas the diffuse scattering of light by finely suspended particulate matter is a non-linear function of particle size and concentration as well as wavelength. Such suspension, therefore, will introduce an error in the analysis results, unless time-consuming and complex (and oftentimes inaccurate) corrections are made for the diffusely scattered radiation energy components. In addition, a wide variety of fluid samples, for example, heavy process food syrups, ice creams or the like, do not transmit sufficient radiation energy to be appropriately processed in accordance with conventional transmission spectroscopy techniques and, hence, require special sample processing, such as dilution, with attendant introduction of further possibility of error.

Also, a wide variety of sample cells are known for use in the analysis of generally solid samples by conventional reflectance spectroscopy techniques. By such techniques, solid samples, generally reduced to a powdered or finely ground consistency, are illuminated by a source of spectral radiation and analyzed for their surface spectral reflectance properties. Light striking and penetrating the sample surface is partially absorbed in accordance with the concentration of sample constituents and their spectral absorbance characteristics; also, such light is diffusely scattered in a similar manner as with turbid liquid samples, into forward and back-scatter components. It is the back-scatter component, selectively attenuated by sample spectral absorbance characteristics, which is measured in a reflectance instrument and used to determine constituent concentration. However, the forward-scatter component is lost by absorbtion within the sample and, hence, not available to determine constituent concentration, although such component contains worthwhile information. Such sample cells would be generally inapplicable for use in the analysis of fluid samples, wherein the spectral reflective surface properties per se of the sample are not indicative of, for example, the concentration of a particular sample constituent.

In addition, and because of the basic differences in optical requirements between transmission and reflectance spectroscopy, currently available spectroscopy instruments are, in general, limited to only one type of measurement or would require complicated and costly accessory equipment for conversion from one type of measurement to the other. Also, because of the limitations set forth hereinabove, a wide variety of existing semi-liquids or semi-solids simply cannot be conveniently analyzed with suitable precision by either existing transmission spectroscopy or reflectance spectroscopy instruments.

OBJECTS OF THE INVENTION

It is an object of this invention to provide a new and improved fluid sample cell which enables the precise analysis of fluid samples by reflectance techniques, for a constituent of interest or other such physical chemical or optical property of the sample.

Another object of this invention is the provision of a fluid sample cell which enables the precise, spectroscopic quantitative analysis of a very wide variety of fluid samples of markedly different turbidities.

Another object of this invention is the provision of a fluid sample cell which enables the precise, spectroscopic quantitative analysis of a wide variety of fluid samples which, because of their opaqueness, cannot be accurately measured by conventional transmission spectroscopy and which, because of their non-solid state, cannot be accurately measured by conventional reflectance spectroscopy.

Another object of this invention is to provide a new and improved fluid sample cell which enables the precise quantitative analysis of both clear and turbid fluid samples by measurement of both the transmitted attenuated radiation due to sample absorbance and both the forward and backward diffusely scattered radiation due to sample turbidity, such that the measurement is independent of variations in turbidity, except for any spectrally absorptive effects of the particulate matter in the sample.

Another object of this invention is the provision of a sample cell which insures accurate fluid sample analysis despite the presence of some quantity of air bubbles in the sample.

A further object of this invention is the provision of a sample cell which is of relatively simple and inexpensive construction and which may be readily and conveniently disassembled for periodic cleaning.

A still further object of this invention is the provision of a sample cell, as above, which is particularly adaptable for use in automated, continuous-flow sample analysis systems.

SUMMARY OF THE DISCLOSURE

As disclosed herein, the new and improved fluid sample cell of our invention comprises a sample compartment of precisely determined depth bounded by opposed surfaces of a transparent window and a diffuse reflector, for example, a diffuse mirror, without appreciable spectral-absorbant characteristics. Access ports are provided to enable the flow of fluid samples into and out of the sample compartment. Preferably, the mirror surface is configured to maintain any air bubbles present in the fluid sample without the viewing area. In operation, the sample portion within the viewing area of the sample compartment is irradiated with radiation energy at a selected wavelength(s). A measurement is taken of the total diffuse reflected radiation energy from the sample, which is composed of: radiation transmitted through the sample and diffusely reflected back from the diffuse mirror; radiation which is scattered by particles in the sample in a forward direction and diffusely reflected back from the diffuse mirror; and radiation which is diffusely scattered by the sample in a backward direction, without reflection off the diffuse mirror. Each of these radiations will have undergone attenuation by the fluid sample in accordance with the spectral absorption characteristics of the sample constituents, concentration of sample constituents, and actual path length traversed through the sample, thus permitting a precise quantitative analysis of the sample.

DESCRIPTION OF THE DRAWINGS

The above and other significant objects and advantages of our invention are believed made clear by the following detailed description thereof taken in conjunction with the accompanying drawings wherein;

FIG. 1 is a top view of a fluid sample cell constructed and operative in accordance with the teachings of our invention;

FIG. 2 is a top view of the fluid sample cell of FIG. 1 with the cover removed for purposes of illustration; and FIG. 3 is a cross-sectional view taken generally vertically along line 3—3 in FIG. 1.

DETAILED DESCRIPTION OF THE INVENTION

Referring now to the drawings, the fluid sample cell is indicated generally at 10 and comprises a generally cup-shaped body member 12 and an annular cover member 14. The body member 12 and cover member 14 are complementally threaded, as indicated at 16 in FIG. 3. A circular viewing aperture, as indicated at 18, is defined in cover member 14 and a circular access aperture, as indicated at 20, is formed as shown centrally of body member 12 at the bottom wall thereof.

A generally circular diffuse reflector or mirror 22 is fabricated from a ceramic or other suitable material of appropriate light dispersing characteristics to insure little, if any, spectral absorption by the mirror. Diffusing mirror 22 may, for example, exhibit the optical and physical characteristics of the ceramic spectral reflectance standard, disclosed in U.S. Pat. No. 4,047,032, assigned to a common assignee. As utilized herein, diffuse mirror 22 comprises a raised annular mounting ridge 24 which extends, as seen in FIG. 3, from the upper, reflecting surface 25 of the mirror. Further, diffuse mirror 22 comprises an annular groove 26 for the mounting of an O-ring seal or gasket 28; stepped, diametrically opposed access ports 30 and 32, as best seen in FIG. 3; and an annular access groove 34 which connects said access ports, as best seen in FIG. 2. A generally circular, transparent window is indicated at 36 and overlies the diffuse mirror 22, as best seen in FIG. 3.

Diffuse mirror 22, O-ring 28 and window 36 are disposed, as shown in FIG. 3, within body member 12, and the cover member 14 is screwed tightly onto body member 12 to force the lower annular surface portion of the window 36 tightly against the upper surface of the raised annular mounting ridge 24. The attendant compression of the O-ring 28 forms a fluid-tight flow cell sample compartment. The raised annular ridge 24 precisely predetermines the length of the light path through sample compartment 38, as indicated at l in FIG. 3. Preferably, this path length l is made as short as possible to insure that the operating characteristics of cell 10 fall within the signal-to-noise ratio bounds of radiation-energy detecting and processing equipment, and to insure that the radiation energy reflected back from the diffuse mirror 22 of cell 10, as described hereinbelow, will always traverse a constant path length, subject to internal scattering effects.

Fluid inlet and outlet conduits 31 and 33 are connected to access ports 30 and 32, respectively, at the bottom of diffuse mirror 22, as seen in FIG. 3, to flow successive fluid samples into and from the sample compartment 38. Of particular significance is the fact that any air bubbles, despite determined efforts to avoid the same, present in the fluid sample, due to surface tension, will follow the path of least resistance and flow into and along access groove 34 upon sample entry into sample compartment 38. Thus, as access groove 34 is located without the viewing area defined by aperture 18 in cover 14, as shown in FIGS. 1 and 3, any air bubbles in the fluid sample will not interfere with the accuracy of the analysis.

For purposes of completeness of description of operation, a source of radiation of appropriate wavelength(s), for example in the near infrared region, is indicated schematically at 40. Also, an optical integrating sphere 42 and radiation detectors, indicated schematically at 44 and 46, respectively, are disposed to receive diffused radiation redirected from the fluid sample cell 10, when irradiated by radiation source 40. A signal processor 57 converts the signal output of the radiation detectors 44 and 46 to a reflectance value, which is used to compute the concentration or magnitude of the constituent or property of the sample, and a display device 58 communicates this output information.

A typical utilization of the sample cell 10 would, for example, involve the operative incorporation thereof in an infrared automated sample analysis system of the type disclosed in co-pending application for the United States Patent Application Ser. No. 15,017 filed Feb. 26, 1979 by J. F. X. Judge, et al., and assigned to a common assignee.

In operation, fluid sample compartment 38 of the sample cell 10 is filled along access port 30 with a fluid sample 50, to be spectroscopically, quantitatively analyzed with regard to a particular constituent thereof, for example, ice cream to be analyzed for fat content taking the form of fine globules in a generally aqueous solution. Radiation of appropriate wavelength, for example a narrow band within the range of 1.4 to 2.5 microns, is directed from radiation source 40 through an opening 43 in integrating sphere 42, through viewing aperture 18 and normal to the surface of mirror 22. Sample cell 10 exhibits the characteristics of a diffuse source of radiation, which is proportional to the intensity of the incident radiation from source 40, the diffuse reflectance characteristics of the fluid sample 50 and the spectral absorption characteristics of the fluid sample 50. The spectral absorption characteristics would be present only if sample 50 is sufficiently transmissive of radiation, so as to allow the same to be reflected back from mirror 22 into the integrating sphere 42. More specifically, and depending upon the optical transmission and-/or diffuse reflectance characteristics of the fluid sample 50, radiation from source 40 incident, as illustrated by beams 51, upon the sample cell through viewing aperture 18 in cover member 14 will be:

(a) partly reflected in substantially specular manner from transparent window 36, as illustrated by beams 52 in FIG. 3. Such reflected radiation is rejected, as it is not reflected within the integrating sphere 42, so as to be incident on radiation detectors 44 and 46. This reflected radiation contains no information relevant to the analysis of the sample constituent of interest;

(b) partly diffusely reflected from sample 50, as illustrated by beams 54 in FIG. 3, back into the optical integrating sphere 42 for detection by radiation detector 44; and (c) partly transmitted through the sample 50 and reflected from the reflective surface 25 of diffuse mirror 22, as illustrated by beams 56 in FIG. 3, back into the optical integrating sphere 42 for detection by radiation detectors 44 and 46.

By way of further explanation, in those instances wherein sample 50 is relatively clear, the major portion of the radiation energy emitted from the irradiated sample cell 10 would be constituted primarily by radiation energy diffused and reflected by mirror 22, as illustrated by beam 56. Conversely, in those instances wherein sample 50 is relatively turbid, the major portion of the radiation energy emitted from the irradiated sample cell 10 would be constituted primarily by radiation energy diffused and scattered from within sample 50, as illustrated by beam 54. In those instances wherein the sample is only quasi-turbid, the radiant energy emitted from the irradiated cell would be comprised of diffused radiant energy diffused and reflected by mirror 22 and scattered within sample 50.

Sequential irradiation as above of the fluid sample 50 with radiation at a predetermined number of different predetermined wavelengths is conducted in accordance with the spectral absorbance characteristics of the sample and of the particular sample property or constituent(s) of interest, and in accordance with the overall diffusivity of the sample. Each radiation wavelength is selected to provide an optimum measurement of the absorption and/or diffusivity of the sample in accordance with spectral absorption characteristics of the sample with respect to the particular constituent to be analyzed. Thereafter, the levels of the reflected radiation, as detected by radiation detectors 44 and 46, are utilized to compute the concentration of the particular sample constituent of interest in manner, for example, as fully disclosed in said co-pending application for U.S. patent Ser. No. 15,017.

Following spectroscopic, quantitative sample analysis as above, it will be understood that the next of a series of fluid samples to be analyzed would be flowed into sample compartment 38, by means of an appropriate pumping system, not shown but indicated by arrow 59, through inlet conduit 31 and access port 30 to displace the analyzed sample from the said sample compartment 38 through access port 32 and outlet conduit 33. The sample analysis procedure, as described, would be repeated on the newly introduced sample. Preferably, a suitable quantity of wash liquid is passed through sample compartment 38 before loading of the next sample so as to prevent inter-sample contamination, in accord with conventional continuous-flow analytical systems, for example, as described in U.S. Pat. No. 3,134,263, assigned to a common assignee.

Of particular significance is the fact that the incident radiation returned and detected, as described, by the optical integrating sphere 42 and radiation detectors 44 and 46, is composed of a purely transmitted component, which is attenuated in precise proportion to the spectral absorbance characteristics of the sample, as would occur in a conventional transmission instrument and both forward- and backward-scattered components, which are also attenuated in precise proportion to the spectral absorbance characteristics of the sample, but which are not normally measured in conventional transmission instruments with any degree of precision. Also, the forward-scatter component is not normally measured in conventional reflectance instruments.

The resulting measurement of the spectral absorbance characteristics of the sample is made substantially without regard to whether the fluid sample of interest is optically transmitting, optically diffuse, or exhibits any possible combination of those optical characteristics. By providing for precise measurements of both the optical reflectance and optical transmission characteristics of the sample in the same sample cell, precise quantitative analysis of fluid samples is achieved substantially without regard to variations in sample turbidity, whereby a particularly wide range of fluid samples of markedly different turbidities may be precisely quantitatively analyzed in the same sample cell. It should be understood that use of the term "fluid sample" in this disclosure is by no means intended as limitative to freely flowing liquid or gaseous samples, but rather, encompasses a wide range of samples including semi-solids in the nature of extremely viscous syrups and limited to the capability of such samples to be flowed into and out of the sample compartment 38 of the fluid sample cell 10.

The construction and assembly, as described, of the sample cell 10 greatly facilitates periodic cleaning thereof, as may be required, to remove residues from the sample compartment 38. More specifically, cover member 14 would be removed by unscrewing from body member 12, to allow full access to sample compartment 38 and diffuse mirror 22 for complete cell cleaning.

Various changes may, of course, be made in the disclosed embodiment of our invention without departing from the spirit and scope thereof as defined in the appended claims.

What is claimed is:

1. A fluid sample cell for the spectroscopic analysis of a fluid sample, comprising: a sample compartment formed in said cell for the containment of a fluid sample, said compartment being defined on opposite sides by a radiation energy-transmitting window and a diffuse reflector spaced from said window, and means for supporting opposing surfaces of said window and said diffuse reflector in spaced fashion, said diffuse reflector being adapted to redirect light incident thereon through a fluid sample contained therebetween and said window, whereby all of said redirected light passing through said window has the character of being diffusely reflected.

2. The fluid sample of claim 1, further comprising inlet and outlet ports for passing successive fluid samples into and out of said compartment.

3. The fluid sample cell of claim 1, wherein said opposing surfaces of said window and said diffuse reflector are planar and are supported by said supporting means in spaced parallel fashion, so as to define a substantially constant sample path length through said sample in a direction normal to said opposing surfaces.

4. The fluid sample cell of claim 2, further comprising: means defining a viewing area through said window, said inlet and outlet ports being disposed outside said viewing area and extending into said sample compartment, and an access groove extending between said inlet and outlet ports and disposed outside said viewing area.

5. A spectroscopic analysis apparatus, comprising: a fluid sample cell including a sample compartment for the containment of a fluid sample to be analyzed, said compartment being defined by a radiation-transmitting window and a diffuse reflector spaced from said window, opposing surface portions of said window and said diffuse reflector being supported in spaced fashion, inlet and outlet ports extending into said compartment for passing successive fluids samples, in turn, through said compartment, a radiation energy source for directing energy through said window and into said compartment, and means for collecting radiation scattered, whether in a forward or back direction, and radiation transmitted by said sample contained within said compartment, at least a portion of said forward scattered and transmitted radiation being reflected back from said diffuse reflector and through said sample, so as to minimize the effects of variations in light scattering on the accuracy of the spectroscopic measurement.

6. The spectroscopic analysis apparatus of claim 5, wherein opposing surface portions of said window and said diffuse reflector are planar and are supported in spaced parallel fashion, so as to define a constant sample path length in a direction normal to said opposing surfaces.

7. The spectroscopic analysis apparatus of claim 5, wherein said opposing surface portions of said window and said diffuse reflector are substantially planar.

8. The spectroscopic analysis apparatus of claim 5, wherein said collecting means comprises a radiation-integrating arrangement, and detector means responsive to radiation which has been integrated by said arrangement.

9. The spectroscopic analysis apparatus of claim 8, further comprising: signal processing means responsive to said detector means, and display means responsive to said processing means.

10. The spectroscopic analysis apparatus of claim 5, further comprising: means disposed over said window for defining a viewing area through said chamber, opposing surfaces of said window and diffuse reflector outside of said viewing area being spaced at least in excess of said sample path length.

11. A method for the spectroscopic analysis of a property of a fluid sample, comprising the steps of: locating a fluid sample between a radiant energy-transmitting window and a diffuse reflector, said window and said diffuse reflector being supported in spaced fashion, for irradiating said fluid sample with selected wavelengths of radiant energy, collecting at least a representative portion of radiation scattered, whether in a forward or backward direction, and radiation transmitted by said fluid sample, at least a portion of said forward scattered and transmitted radiation being reflected back from said diffuse reflector and through said fluid sample for collection, integrating said collected radiation, and generating a signal in accordance with said collected radiation, as an indication of said property, so as to minimize the effects of variations in light scattering on the accuracy of the spectroscopic measurement.

* * * * *